United States Patent
Choi

(10) Patent No.: US 8,287,775 B2
(45) Date of Patent: *Oct. 16, 2012

(54) PHOTOCHROMIC MATERIAL

(75) Inventor: Dong Hoon Choi, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 4 days.

This patent is subject to a terminal disclaimer.

(21) Appl. No.: 12/707,498

(22) Filed: Feb. 17, 2010

(65) Prior Publication Data

US 2011/0198546 A1    Aug. 18, 2011

(51) Int. Cl.
  G02B 5/23      (2006.01)
  C07D 265/12    (2006.01)
  C07D 265/00    (2006.01)

(52) U.S. Cl. ........ 252/586; 252/582; 252/600; 436/164; 544/71; 544/89; 548/509

(58) Field of Classification Search .................. 252/586, 252/582, 600; 264/1.1, 1.7, 1.8, 255, 245, 264/246; 525/934; 427/162, 164; 436/164; 544/71, 89; 548/509
See application file for complete search history.

(56) References Cited

U.S. PATENT DOCUMENTS

| | | | |
|---|---|---|---|
| 6,068,797 A | 5/2000 | Hunt | |
| 2003/0045714 A1 | 3/2003 | Melzig et al. | |
| 2008/0055686 A1 | 3/2008 | Erben et al. | |
| 2009/0032782 A1 | 2/2009 | Kim et al. | |

FOREIGN PATENT DOCUMENTS

| | | | |
|---|---|---|---|
| EP | 1433620 | | 6/2004 |
| JP | 3-81278 | * | 4/1991 |
| JP | 5-43870 | | 2/1993 |
| JP | 5-65477 | | 3/1993 |
| JP | 7-228584 | | 8/1995 |
| WO | WO 2010/020770 | | 2/2010 |

OTHER PUBLICATIONS

Guglielmetti, R., 'New polyphotochromic system involving spirooxazine and/or chromene joined by a (Z) ethylenic bridge', Advances in Colour Science and Technology, 2002, vol. 5 (4), pp. 113-116.
International Search Report for PCT/KR2010/009127 mailed Apr. 2, 2011.
International Search Report for PCT/KR2010/009128 mailed Apr. 2, 2011.
Ortica, F. et al., 'Photokinetic behaviour of biphotochromic supra molecular systems Part 2. A bis-benzo-[2H]-chromene and a spirooxazine-chromene with a (Z-)ethenic bridge between each moiety', J. Photochem. Photobiol. A: Chemistry, 2001, vol. 139, pp. 133-141.
U.S. Appl. No. 12/683,238, filed Jan. 6, 2010, Choi.
Yip, W. T. et al., 'Energy Transfer in Bichromophoric Molecules: The Effects of Symmetry and Donor/Acceptor Energy Gap', J. Phys. Chem. A, 1999, vol. 103, pp. 10-20.
Tsivgoulis, Gerasimo M. et al., "Photonic Molecular Devices: Reversibly Photoswitchable Fluorophores for Nondestructive Readout for Optical Memory", Angew. Chem. Int. Ed. Engl. 1995, 34, No. 10, pp. 119-1121.
U.S. Appl. No. 12/683,238, Mar. 18, 2011, Office Action.
U.S. Appl. No. 12/683,238, May 17, 2011, Office Action.
U.S. Appl. No. 12/683,238, Oct. 20, 2011, Office Action.
U.S. Appl. No. 12/683,238, Mail Date Jun. 29, 2012, Notice of Allowance.

* cited by examiner

Primary Examiner — Bijan Ahvazi
(74) Attorney, Agent, or Firm — Workman Nydegger

(57) ABSTRACT

Photochromic dyes are disclosed. A photochromic dye can include a first photo-reactive group and a second photo-reactive group. A first photochromic reaction can be induced in the first photo-reactive group of the photochromic dye by radiation having a first intensity, and a second photochromic reaction can be induced in the second photo-reactive group of the photochromic dye by radiation having a second intensity. The second intensity may be greater than the first intensity.

28 Claims, No Drawings

PHOTOCHROMIC MATERIAL

TECHNICAL FIELD

This disclosure relates generally to photochromic materials.

BACKGROUND

A number of photochromic materials are used in many industrial fields. The absorption spectra and thus the color of photochromic materials can change as a result of the absorption of electromagnetic radiation (e.g., visible or UV light).

Many photochromic materials possess color change properties due to the phenomenon of photochromism. Photochromism refers to a reversible, light-induced transformation of a chemical compound between at least two forms. The at least two forms inherently have different absorption spectra, so they exhibit different colors. A photochromic dye is a photochromic material exhibiting light-dependent color change properties. Absorption of light radiation can reversibly transform a photochromic dye between two forms having different absorption spectra, so as to exhibit different colors.

SUMMARY

One embodiment of the disclosure describes a photochromic dye. The photochromic dye can include a first photo-reactive group and a second photo-reactive group. In one aspect, a first photochromic reaction can be induced in the first photo-reactive group by radiation having a first intensity, and a second photochromic reaction can be induced in the second photo-reactive group by radiation having a second intensity.

According to another embodiment, a photochromic dye is described. The photochromic dye can include a first photo-reactive group that includes a first photo-reactive moiety and a second photo-reactive group that includes a second photo-reactive moiety. In one aspect, a first photochromic reaction can be induced in the first photo-reactive moiety by radiation having a first intensity, and a second photochromic reaction can be induced in the second photo-reactive moiety by radiation having a second intensity, with the second intensity being greater than the first intensity.

According to yet another embodiment, photochromic composition is described. In one aspect, the photochromic composition can include at least one material selected from the group consisting of a polymer, an oligomer, a monomer, or a mixture thereof, and at least one photochromic dye incorporated into at least a portion of the material. In one aspect, the at least one photochromic dye can include a first photo-reactive group and a second photo-reactive group. In one aspect, a first photochromic reaction can be induced in the first photo-reactive group by radiation having a first intensity, and a second photochromic reaction can be induced in the second photo-reactive group by radiation having a second intensity.

According to still yet another embodiment, an optical article is described. In one aspect, the optical article can include at least one optical article selected from the group consisting of ophthalmic elements, display elements, windows, mirrors, liquid crystal cell elements, and combinations thereof, and at least one photochromic dye incorporated into at least a portion of the optical article. In one aspect, the at least one photochromic dye can include a first photo-reactive group and a second photo-reactive group. In one aspect, a first photochromic reaction can be induced in the first photo-reactive group by radiation having a first intensity, and a second photochromic reaction can be induced in the second photo-reactive group by radiation having a second intensity.

The foregoing summary is illustrative only and is not intended to be in any way limiting. In addition to the illustrative aspects, embodiments, and features described above, further aspects, embodiments, and features will become apparent by reference to the following detailed description.

DETAILED DESCRIPTION

I. Introduction and Definitions

In the following detailed description, reference is made to the accompanying structural formulas, which form a part hereof. In the structural formulas, similar symbols typically identify similar components, unless context dictates otherwise. The illustrative embodiments described in the detailed description, structural formulas, and claims are not meant to be limiting. Other embodiments may be utilized, and other changes may be made, without departing from the spirit or scope of the subject matter presented here.

A photochromic dye according to the present disclosure refers to a photochromic material (e.g., a chemical dye) that can exhibit two or more color changes as the intensity of irradiation changes. A photochromic dye as described herein can be formed by linking two or more photo-reactive groups having different reactivities together in a single molecule.

The term "photo-reactive group" as used herein means any substance having photo-reactive properties. Transformation of a photo-reactive group from one form to another can be induced by absorption of electromagnetic radiation (e.g., UV or visible light radiation). Some common photo-reactive transformations include, but are not limited to, ring-opening or closing reactions, pericyclic reactions, cis-trans isomerizations, intramolecular hydrogen transfer, intramolecular group transfers, dissociation processes and electron transfers.

In one aspect, a photo-reactive group can include a photochromic group. In one aspect, a photochromic reaction can be a color-change reaction that occurs in a photochromic group. As such, the transformation from one form to the other can include a photochromic reaction that causes or induces a change in the absorption spectrum of the dye such that the two forms exhibit different colors.

The term "photochromic moiety" as used herein refers to a part or portion of a photo-reactive group, in which a photochromic reaction occurs in order to undergo a reversible photochromic transformation from one form to another.

The term "ring-opening or closing reaction," as used herein, refers to a ring-opening reaction or ring-closing reaction that happens when a photochromic group absorbs light radiation. According to the species of the photochromic group, a ring-opening reaction or a ring-closing reaction takes place. For example, spiropyrans and spirooxazines undergo a ring-opening reaction in response to light radiation, whereas diarylethenes and fulgides undergo a ring-closing reaction in response to light radiation.

The term "conjugation system" as used herein refers to a system where atoms covalently bond with alternating single and double bonds. In one aspect, a first photochromic reaction, as disclosed herein, can include a modification of a first conjugation system in a first photo-reactive group, and a second photochromic reaction can include modification of a second conjugation system in a second photo-reactive group. For example, a photochromic reaction induced by absorbance of a photon of light having a given wavelength and/or intensity can induce a transformation in a photo-reactive group from a first conjugation system having a first conjugation bond length to a second conjugation system having a second (e.g., longer) conjugation bond length. It is generally the case that the absorptions spectra of molecules and thus their color changes as the conjugation bond length changes. In general, conjugation systems having less than eight conjugated double bonds only absorb light in the ultraviolet region and are colorless to the human eye. With the addition of additional conjugated double bonds (i.e., an increase in the conjugation bond length), the conjugation system absorbs photons of longer wavelength (and lower energy), eventually resulting in the absorbance of photons in the visual range of the human eye.

Thus, the photochromic reactions discussed herein induce the transformation of photochromic dyes from a first isomer having a first conjugation bond length to a second isomer having a second conjugation bond length, or from a second isomer having a second conjugation bond length to a third isomer having a third conjugation bond length. With the increase in conjugation bond length, the photochromic dyes disclosed herein can absorb photons of longer wavelengths. As such, a colorless photochromic dye can change to a colored photochromic dye (e.g., colorless to blue), or a colored photochromic dye can change to a photochromic dye having a different color (e.g., blue to red).

For example, Scheme I below shows a ring-opening reaction of a spirooxazine in response to UV light irradiation. The spirooxazine shown in Scheme I includes a photo-reactive group and the compound can be termed "photochromic" because the spirooxazine changes its absorption properties, and thus its color, in response to UV irradiation. The spiro form of an oxazine is a colorless leuco dye having a conjugated oxazine and another conjugated aromatic portion separated by an $sp^3$ hybridized spiro carbon (represented by *). After irradiation with UV light, the bond between the spiro carbon and the oxazine breaks, opening the ring. As a result, the spiro carbon switches to an $sp^2$ hybridization state and becomes planar, the aromatic group rotates, and an extended conjugation system is formed. The formation of the extended conjugation system allows the molecule to absorb photons of visible light, and therefore appear colorful. When the UV source is removed, the molecule will gradually relax to its ground state, the carbon-oxygen bond reforms, the spiro-carbon becomes $sp^3$ hybridized again, and the molecule returns to its colorless state.

[Scheme I]

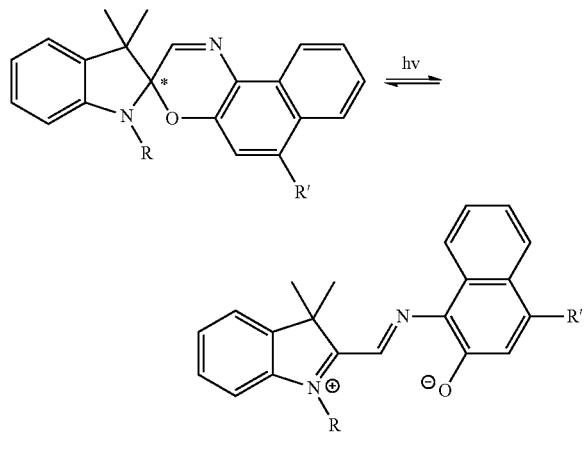

The term "light radiation" as used herein refers to electromagnetic radiation such as, but not limited to, ultraviolet and visible radiation that is capable of causing a photo-reactive group to transform from one form to another.

The reactivity of a photochromic reaction is related to the molar absorptivity of the photochromic groups. The term "molar absorptivity" as used herein refers to a measurement of how strongly a chemical substance absorbs light at a given wavelength. It is an intrinsic property of the substance. The molar absorptivity ($\epsilon$) of a material is related to the absorbance of the material by the following equation:

$$\epsilon = A/(c \times l)$$

wherein "A" is the absorbance of the material at a particular wavelength, "c" is the concentration of the material in moles per liter (mol/L) and "l" is the path length (or cell thickness) in centimeters.

As used herein, the terms "intensity" and "intensity of light radiation" refer to a strength of light. Strength of light can refer light power (e.g., energy transferred by light radiation) per unit area (e.g., mW/cm$^2$). Strength of light can also refer to light having a given power shining on an area for a period of time.

II. Photochromic Dyes

Embodiments of the present disclosure relate to photochromic dyes. Photochromic dyes are dyes that exhibit the ability to reversibly change color in response to absorption of electromagnetic radiation. The photochromic dyes disclosed herein possess at least two photo-reactive groups, allowing the photochromic dyes to reversibly transform between at least two forms having at least two different colors.

In one aspect of the present disclosure, a photochromic dye includes a first photo-reactive group and a second photo-reactive group. A first photochromic reaction can be induced in the first photo-reactive group by radiation having a first intensity, and a second photochromic reaction can induced in the second photo-reactive group by radiation having a second intensity.

In one aspect, the photochromic dye is configured such that the first photochromic reaction can occur before the second photochromic reaction. In another aspect, the photochromic dye is configured such that the first photochromic reaction is induced by light radiation having the first intensity and the second photochromic reaction is induced by light radiation having the second intensity, the second intensity being greater than the first intensity. That is, the first photochromic reaction is induced under irradiation and the second photochromic reaction is subsequently induced under continued irradiation as the intensity of the incident radiation increases.

To illustrate the formation of a conjugation system that allows a molecule to appear colorful, Scheme I will be referred to below.

[Scheme I]

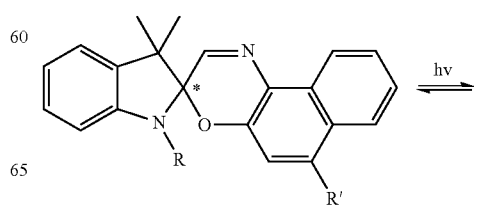

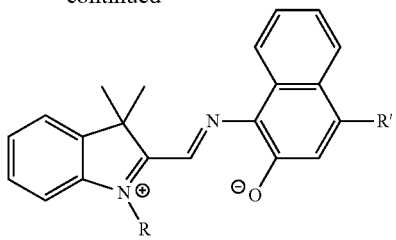

In the absence of irradiation, the spirooxazine shown on the left-hand portion of Scheme I includes two separated portions having conjugated double bonds. That is, the conjugated systems of the oxazine on one end of the molecule and the benzene ring on the other end of the molecule are separated by the "spiro" carbon (indicated by *). The presence of the spiro linkage in between the conjugated systems prevents extended overlap of the pi-orbitals from one end of the molecule to the other. As a result, the non-irradiated from of the spirooxazine is colorless.

In response to irradiation, however, the bond between the spiro-carbon and the oxazine breaks, and a conjugation system forms extending from one end of the molecule to the other. In such a state, the oxazine is able to absorb visible light and appear colorful.

In contrast to the spirooxazine discussed above, the photochromic dyes disclosed herein can include a first photo-reactive group having a first conjugation system and a second photo-reactive group having a second conjugation system. In one aspect, the first conjugation system can be formed when the first photochromic reaction is induced, and the second conjugation system can be formed when the second photochromic reaction is induced. In one aspect, the first conjugation system has a first conjugation bond length and the second conjugation system has a second conjugation bond length that is longer than the first conjugation bond length. That is, additional double bonds in the conjugation system allow the molecule to absorb photons of longer wavelength (and lower energy), which eventually results in the compound having a color that can be seen by the human eye.

In one embodiment of the presently disclosed photochromic dyes, two photo-reactive groups have different degrees of molar absorptivity. As a rule, the higher the molar absorptivity of a material, the more radiation the material will absorb on a per molecule basis. That is, the higher the molar absorptivity of a material, the more easily a photochromic reaction will take place, whereas the lower the molar absorptivity of a substance, the more difficult it is for a photochromic reaction to take place. If the difference in molar absorptivity between multiple photochromic groups is large, sequential conversion of the photo-reactive groups will be efficient. That is, a first photochromic reaction will occur in response to absorbance of radiation having a first intensity and a second photochromic reaction will occur in response to absorbance of radiation having a second, higher intensity. In addition, the timing of the two reactions can be well separated gradually increasing the intensity of the incident radiation.

As such, in one embodiment, the difference of molar absorptivity between the first photo-reactive group and the second photo-reactive group being greater than or equal to about 5000 L/mol such that the first photochromic reaction will occur in response to irradiation by relatively low intensity radiation and the second photochromic reaction will occur in response to irradiation by relatively higher intensity radiation. In another aspect, the difference of molar absorptivity between the first photo-reactive group and the second photo-reactive group being greater than or equal to about 5500 L/mol, or about 6000 L/mol, or about 6500 L/mol, or about 7000 L/mol, or about 7500 L/mol, or about 8000 L/mol, or about 8500 L/mol, or about 9000 L/mol, or about 9500 L/mol, or about 10,000 L/mol, or about 10,500 L/mol, or about 11,000 L/mol, or about 11,500 L/mol, or about 12,000 L/mol, or about 12,500 L/mol, or about 13,000 L/mol, or about 13,500 L/mol, or about 14,000 L/mol, or about 14,500 L/mol, or about 15,000 L/mol, or about 15,500 L/mol, or about 16,000 L/mol, or about 16,500 L/mol, or about 17,000 L/mol, or about 17,500 L/mol, or about 18,000 L/mol, or about 18,500 L/mol, or about 19,000 L/mol, or about 19,500 L/mol, or about 20,000 L/mol.

In another embodiment, the first photo-reactive group can have a molar absorptivity of about 20,000 L/mol to about 30,000 L/mol, and the second photo-reactive group can have a molar absorptivity of about 10,000 L/mol to about 15,000 L/mol. As such, the first photochromic reaction can occur in response to irradiation by relatively low intensity radiation and the second photochromic reaction can occur in response to irradiation by relatively higher intensity radiation. In another aspect, the first photo-reactive group can have a molar absorptivity of about 21,000 L/mol to about 30,000 L/mol and the second photo-reactive group can have a molar absorptivity of about 10,000 L/mol to about 14,5000 L/mol, or the first photo-reactive group can have a molar absorptivity of about 22,000 L/mol to about 30,000 L/mol and the second photo-reactive group can have a molar absorptivity of about 10,000 L/mol to about 14,000 L/mol, or the first photo-reactive group can have a molar absorptivity of about 23,000 L/mol to about 30,000 L/mol and the second photo-reactive group can have a molar absorptivity of about 10,000 L/mol to about 13,500 L/mol, or the first photo-reactive group can have a molar absorptivity of about 24,000 L/mol to about 30,000 L/mol and the second photo-reactive group can have a molar absorptivity of about 10,000 L/mol to about 13,000 L/mol, or the first photo-reactive group can have a molar absorptivity of about 25,000 L/mol to about 30,000 L/mol and the second photo-reactive group can have a molar absorptivity of about 10,000 L/mol to about 12,500 L/mol, or the first photo-reactive group can have a molar absorptivity of about 26,000 L/mol to about 30,000 L/mol and the second photo-reactive group can have a molar absorptivity of about 10,000 L/mol to about 12,000 L/mol, or the first photo-reactive group can have a molar absorptivity of about 27,000 L/mol to about 30,000 L/mol and the second photo-reactive group can have a molar absorptivity of about 10,000 L/mol to about 11,500 L/mol, or the first photo-reactive group can have a molar absorptivity of about 28,000 L/mol to about 30,000 L/mol and the second photo-reactive group can have a molar absorptivity of about 10,000 L/mol to about 11,000 L/mol, or the first photo-reactive group can have a molar absorptivity of about 29,000 L/mol to about 30,000 L/mol and the second photo-reactive group can have a molar absorptivity of about 10,000 L/mol to about 10,500 L/mol, or the first photo-reactive group can have a molar absorptivity of about 30,000 L/mol and the second photo-reactive group can have a molar absorptivity of about 10,000 L/mol.

In yet another embodiment of the disclosure, the first photochromic reaction can be induced when light having an intensity of about 50 mW/cm$^2$ to about 100 mW/cm$^2$ is absorbed by the first photo-reactive group and the second photochromic reaction can be induced when light having an intensity of about 150 mW/cm$^2$ to about 200 mW/cm$^2$ is absorbed by the second photo-reactive group. As such, the first photochromic reaction can occur in response to irradiation by relatively low intensity radiation and the second photochromic reaction can occur in response to irradiation by relatively higher intensity radiation. In another aspect, the first photochromic reaction can be induced when light having an intensity of about 60 mW/cm$^2$ to about 100 mW/cm$^2$ is absorbed by the first photo-reactive group and the second photochromic reaction can be induced when light having an intensity of about 160 mW/cm$^2$ to about 200 mW/cm$^2$ is absorbed by the second photo-reactive group, or the first photochromic reaction can be induced when light having an intensity of about 70 mW/cm$^2$ to about 100 mW/cm$^2$ is absorbed by the first photo-reactive group and the second photochromic reaction can be induced when light having an intensity of about 170 mW/cm$^2$ to about 200 mW/cm$^2$ is absorbed by the second photo-reactive group, or the first photochromic reaction can be induced when light having an intensity of about 80 mW/cm$^2$ to about 100 mW/cm$^2$ is absorbed by the first photo-reactive group and the second photochromic reaction can be induced when light having an intensity of about 180 mW/cm$^2$ to about 200 mW/cm$^2$ is absorbed by the second photo-reactive group, or the first photochromic reaction can be induced when light having an intensity of about 90 mW/cm$^2$ to about 100 mW/cm$^2$ is absorbed by the first photo-reactive group and the second photochromic reaction can be induced when light having an intensity of about 190 mW/cm$^2$ to about 200 mW/cm$^2$ is absorbed by the second photo-reactive group, or the first photochromic reaction can be induced when light having an intensity of about 100 mW/cm$^2$ is absorbed by the first photo-reactive group and the second photochromic reaction can be induced when light having an intensity of about 200 mW/cm$^2$ is absorbed by the second photo-reactive group.

In yet another embodiment of the disclosure, the wavelengths of light that are absorbed by the photochromic dyes can be about 250 to 400 nm, or about 260 to 390 nm, or about 270 to 380 nm, or about 280 to 370 nm, or about 290 to 370 nm, or about 300 to 370 nm, or about 310 to 370 nm, or about 320 to 370 nm, or about 330 to 370 nm, or about 340 to 370 nm, or about 350 to 370 nm, or about 360 to 370 nm, or about 365 nm.

As can be appreciated from the preceding discussion, when the photochromic dyes disclosed herein are exposed to light with a relatively low intensity of light radiation, the first photo-reactive group, which typically has a higher molar absorptivity, undergoes the first photochromic reaction, e.g., a ring-opening or closing reaction, and/or a cis-trans isomerization. By this first photochromic reaction, the first conjugation system is formed. That is, the conjugation system is extended from one end of the first photochromic compound to the second photo-reactive group. The extended conjugation system formed by the first photochromic reaction allows the dye to absorb photons of longer wavelength, which give the dye its first color.

When exposed to relatively more intense radiation the second photochromic group, which in configured to have a lower molar absorptivity, undergoes the second photochromic reaction, e.g., a ring-opening or closing reaction and/or a cis-trans isomerization. By this second photochromic reaction, the second conjugation system is formed. That is, the conjugation system is extended from the end of the first photochromic group to the end of the second photochromic group. By extending the dye's conjugation system, the dye can absorb photons of longer wavelength, and therefore exhibit another color.

Scheme II shown below represents an example of a sequential photochromic reaction (i.e., a ring-opening reaction) of two photochromic groups of a photochromic dye according to this disclosure.

[Scheme II]

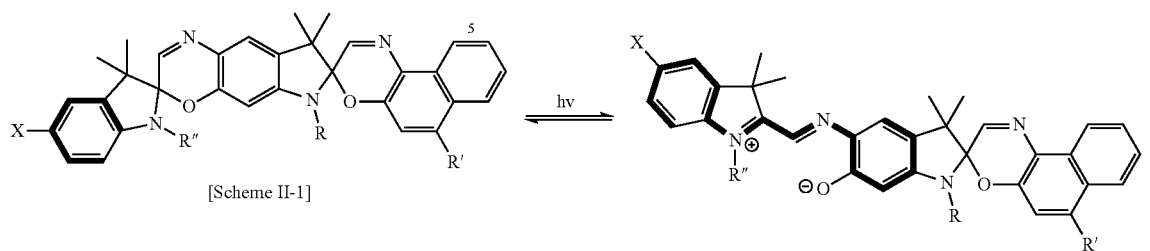

[Scheme II-1]

[Scheme II-2]

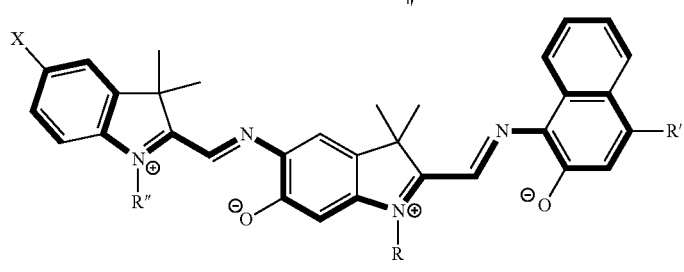

[Scheme II-3]

In scheme II, two spirooxazine photo-reactive groups are linked to form a two color changeable dye. The dye structure shown in Scheme II-1 is colorless because the conjugation systems are separated by spiro carbons and they are too short to absorb visible light. For example, a conjugation system associated with the first photo-reactive group is shown in Scheme II-1 by the bold line. The conjugation system in Scheme II-1 indicated by the bold line includes only three conjugated double bonds, which is too short to allow the compound to absorb visible light and appear colorful.

When the dye is irradiated, however, the first photo-reactive group undergoes the first photochromic reaction. In this scheme, the first photo-reactive group reacts first because it has higher molar absorptivity compared to the second photo-reactive group. As a result of the first photochromic reaction, the conjugation system is extended to the second photo-reactive group (scheme II-2, bold line) to a conjugation bond length of eight conjugated double bonds, which is enough to allow the dye to absorb visible light and exhibit color (e.g., blue).

When the dye is irradiated with light having a relatively higher intensity, is irradiated, the second photo-reactive group undergoes a second ring-opening reaction. As a result of the second photochromic reaction, the conjugation system is extended to the length of the whole molecule (scheme II-3, bold line) to a conjugation bond length of thirteen conjugated double bonds, which is enough to allow the dye to absorb a different (i.e., longer) wavelength of visible light and exhibit a second color (e.g., red).

According to one embodiment, the first and the second photo-reactive groups are at least one selected independently from the group consisting of a spiropyran compound, a spirooxazine compound, a diarylethene compound and a fulgide compound.

Non-limiting examples of photochromic diarylethenes from which the photo-reactive group can be chosen include thiophene perfluoropentenes; benzothiophene perfluoropentenes; benzothiophene maleicanhydrides; benzothiophene cyanoethenes; and benzothiophene sulfone perfluoropetenes.

Non-limiting examples of photochromic fulgides from which the photo-reactive group can be chosen include the 3-furyl and 3-thienyl fulgides and fulgimides.

In one embodiment, the photochromic dye of the present disclosure may include a first photo-reactive group that includes a first photo-reactive moiety and a second photo-reactive group that includes a second photo-reactive moiety. In the photochromic dye, a first photochromic reaction can be induced in the first photo-reactive moiety by radiation having a first intensity, and a second photochromic reaction can be induced in the second photo-reactive moiety by radiation having a second intensity, with the second intensity being greater than the first intensity.

In one embodiment, the photochromic dye can be represented by formula I:

[Formula I]

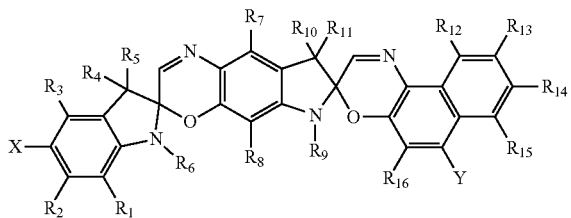

wherein, X and Y independently represent hydrogen, an electron donor group or an electron acceptor group, but if X represents an electron donor group then Y represents hydrogen or an electron acceptor group, and if X represents an electron acceptor group then Y represents hydrogen or an electron donor group; and $R_1$ to $R_{16}$ independently represent hydrogen, a halogen, a substituted or unsubstituted $C_{1-8}$ alkyl, a substituted or unsubstituted $C_{1-8}$ alkoxy, a substituted or unsubstituted $C_{1-8}$ alkenyl, a substituted or unsubstituted $C_{1-8}$ conjugated alkyl, a substituted or unsubstituted aryl group, a substituted or unsubstituted heteroaryl group, or the substituents together form an alkylene or alkenylene chain completing an aryl group. Specifically, said $R_1$ to $R_{16}$ independently represent hydrogen, a halogen, a substituted or unsubstituted $C_{1-6}$ alkyl, a substituted or unsubstituted $C_{1-6}$ alkoxy, a substituted or unsubstituted $C_{1-6}$ alkenyl, a substituted or unsubstituted $C_{1-6}$ conjugated alkyl, a substituted or unsubstituted aryl group, a substituted or unsubstituted heteroaryl group, or the substituents together form an alkylene or alkenylene chain completing an aryl group. More specifically, said $R_1$ to $R_{16}$ independently represent hydrogen, a halogen, a substituted or unsubstituted $C_{1-4}$ alkyl, a substituted or unsubstituted $C_{1-4}$ alkoxy, a substituted or unsubstituted $C_{1-4}$ alkenyl, a substituted or unsubstituted $C_{1-4}$ conjugated alkyl, a substituted or unsubstituted aryl group, a substituted or unsubstituted heteroaryl group, or the substituents together form an alkylene or alkenylene chain completing an aryl group.

Unless otherwise indicated, this disclosure uses definitions provided below.

"Substituted" groups are those in which one or more hydrogen atoms have been replaced with one or more non-hydrogen groups, provided that valence requirements are met and that a chemically stable compound results from the substitution.

"Alkyl" refers to straight chain and branched saturated hydrocarbon groups, generally having a specified number of carbon atoms (i.e., $C_{1-6}$ alkyl refers to an alkyl group having 1, 2, 3, 4, 5, or 6 carbon atoms and $C_{1-12}$ alkyl refers to an alkyl group having 1, 2, 3, 4, 5, 6, 7, 8, 9, 10, 11, or 12 carbon atoms). Examples of alkyl groups include, without limitation, methyl, ethyl, n-propyl, i-propyl, n-butyl, s-butyl, i-butyl, t-butyl, pent-1-yl, pent-2-yl, pent-3-yl, 3-methylbut-1-yl, 3-methylbut-2-yl, 2-methylbut-2-yl, 2,2,2-trimethyleth-1-yl, n-hexyl, and the like.

"Alkoxy" refers to alkyl-O, alkenyl-O, and alkynyl-O. Examples of alkoxy groups include, without limitation, methoxy, ethoxy, n-propoxy, i-propoxy, n-butoxy, s-butoxy, t-butoxy, n-pentoxy, s-pentoxy, and the like.

"Alkenyl" refers to straight chain and branched hydrocarbon groups having one or more unsaturated carbon-carbon bonds, and generally having a specified number of carbon atoms. Examples of alkenyl groups include, without limitation, ethenyl, 1-propen-1-yl, 1-propen-2-yl, 2-propen-1-yl, 1-buten-1-yl, 1-buten-2-yl, 3-buten-1-yl, 3-buten-2-yl, 2-buten-1-yl, 2-buten-2-yl, 2-methyl-1-propen-1-yl, 2-methyl-2-propen-1-yl, 1,3-butadien-1-yl, 1,3-butadien-2-yl, and the like.

"Aryl" refers to monovalent and divalent aromatic groups, respectively, including 5- and 6-membered monocyclic aromatic groups that contain 0 to 4 heteroatoms independently selected from nitrogen, oxygen, and sulfur. Examples of monocyclic aryl groups include, without limitation, phenyl, pyrrolyl, furanyl, thiophenyl, thiazolyl, isothiazolyl, imidazolyl, triazolyl, tetrazolyl, pyrazolyl, oxazolyl, isooxazolyl, pyridinyl, pyrazinyl, pyridazinyl, pyrimidinyl, and the like. The aryl group also includes bicyclic groups, tricyclic groups, etc., including fused 5- and 6-membered rings as described above. Examples of multicyclic aryl groups include, without limitation, naphthyl, biphenyl, anthracenyl, pyrenyl, carbazolyl, benzoxazolyl, benzodioxazolyl, benzothiazolyl, benzoimidazolyl, benzothiopheneyl, quinolinyl, isoquinolinyl, indolyl, benzofuranyl, purinyl, indolizinyl, and the like. The aryl and arylene groups may be attached to a parent group or to a substrate at any ring atom, unless such attachment would violate valence requirements. Likewise, the aryl group may include one or more non-hydrogen substituents unless such substitution would violate valence requirements. Useful substituents include, without limitation, alkyl, alkenyl, alkynyl, haloalkyl, haloalkenyl, haloalkynyl, cycloalkyl, cycloalkenyl, alkoxy, cycloalkoxy, alkanoyl, cycloalkanoyl, cycloalkenoyl, alkoxycarbonyl, cycloalkoxycarbonyl, and halo, as defined above, and hydroxy, mercapto, nitro, amino, and alkylamino.

In one embodiment, the electron donor group may be an amino, an alkylamino, a dialkylamino, an alkyl, an alkoxy, a julolidine or a diphenyl. The electron acceptor group may be a cyano, a nitrogen oxide, a halogen, a trifluoromethyl, a dicyanovinyl or a tricyanovinyl.

In one non-limiting embodiment, the photochromic dye of Formula I may be selected from the group consisting of the following Formula I-1 to I-8:

[Formula I-1]

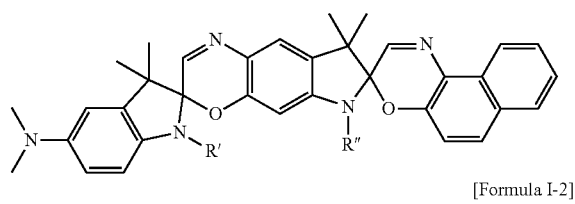

[Formula I-2]

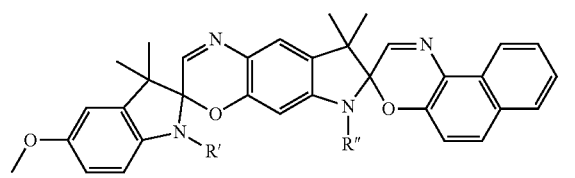

[Formula I-3]

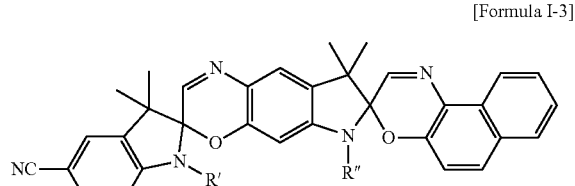

[Formula I-4]

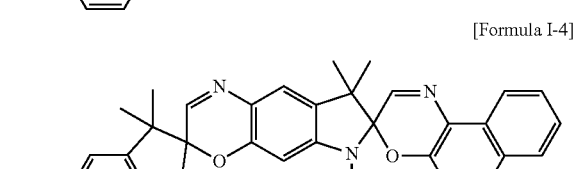

[Formula I-5]

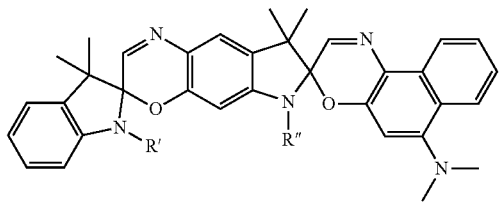

[Formula I-6]

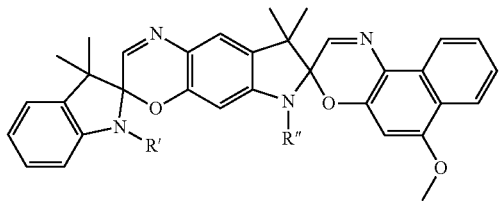

[Formula I-7]

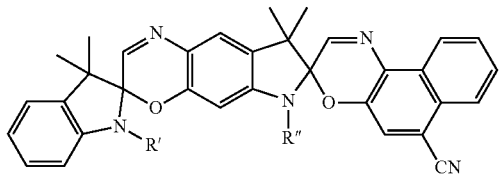

[Formula I-8]

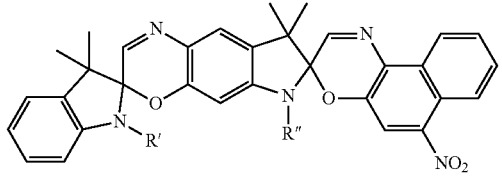

wherein, R' and R" independently represent hydrogen, a halogen, a substituted or unsubstituted $C_{1-8}$ alkyl, or a substituted or unsubstituted $C_{1-8}$ alkoxy. Specifically, R' and R" independently represent hydrogen, a halogen, a substituted or unsubstituted $C_{1-6}$ alkyl, or a substituted or unsubstituted $C_{1-6}$ alkoxy.

Two photo-reactive groups may be linked so as to have a conjugation system between photo-reactive centers. According to non-limiting examples, the photo-reactive groups may be linked to one another directly. Further, the photo-reactive groups may be linked to one another through linkage groups.

In one embodiment, the photochromic dye of the present disclosure may be represented by formula II:

[Formula II]

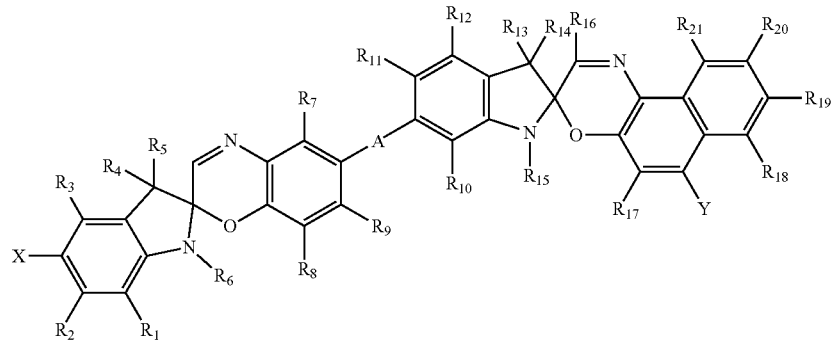

wherein, X and Y independently represent hydrogen, an electron donor group or an in electron acceptor group, but if X represents an electron donor group then Y represents hydrogen or an electron acceptor group, and if X represents an electron acceptor group then Y represents hydrogen or an electron donor group; $R_1$ to $R_{21}$ independently represent hydrogen, a halogen, a substituted or unsubstituted $C_{1-8}$ alkyl, a substituted or unsubstituted $C_{1-8}$ alkoxy, a substituted or unsubstituted $C_{1-8}$ alkenyl, a substituted or unsubstituted $C_{1-8}$ conjugated alkyl, a substituted or unsubstituted aryl group, a substituted or unsubstituted heteroaryl group, or the substituents together form an alkylene or alkenylene chain completing an aryl group; and A represents a single bond,

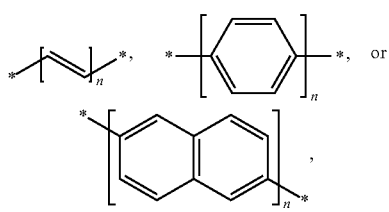

wherein n is 1 to 6, 1 to 4, or 1 to 2. Specifically, said $R_1$ to $R_{21}$ may independently represent hydrogen, a halogen, a substituted or unsubstituted $C_{1-6}$ alkyl, a substituted or unsubstituted $C_{1-6}$ alkoxy, a substituted or unsubstituted $C_{1-6}$ alkenyl, a substituted or unsubstituted $C_{1-6}$ conjugated alkyl, a substituted or unsubstituted aryl group, a substituted or unsubstituted heteroaryl group, or the substituents together form an alkylene or alkenylene chain completing an aryl group. More specifically, said $R_1$ to $R_{21}$ may independently represent hydrogen, a halogen, a substituted or unsubstituted $C_{1-4}$ alkyl, a substituted or unsubstituted $C_{1-4}$ alkoxy, a substituted or unsubstituted $C_{1-4}$ alkenyl, a substituted or unsubstituted $C_{1-4}$ conjugated alkyl, a substituted or unsubstituted aryl group, a substituted or unsubstituted heteroaryl group, or the substituents together form an alkylene or alkenylene chain completing an aryl group.

In one non-limiting embodiment, the photochromic dye of Formula II may be selected from the group consisting of the following Formula II-1 to II-4:

[Formula II-1]

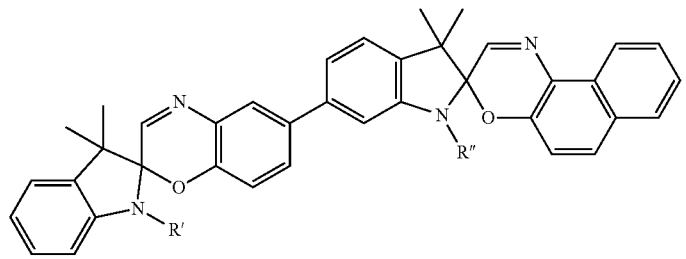

[Formula II-2]

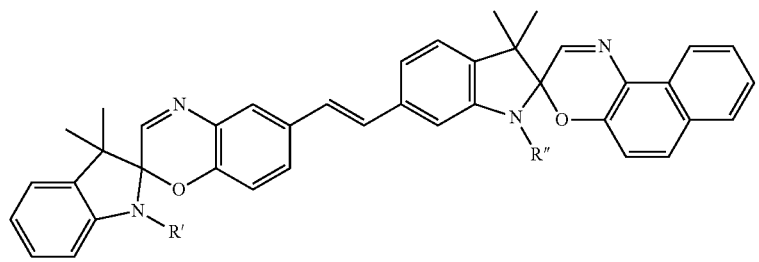

[Formula II-3]

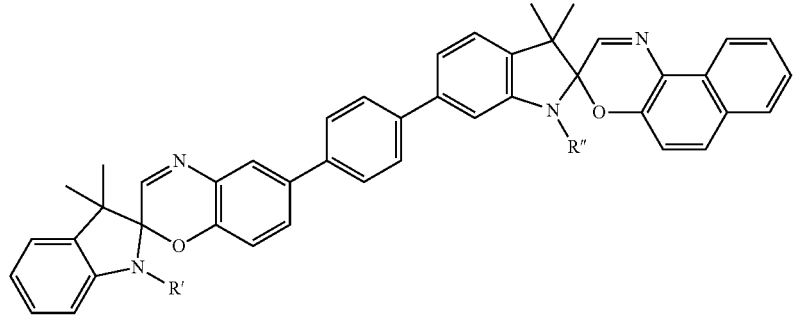

[Formula II-4]

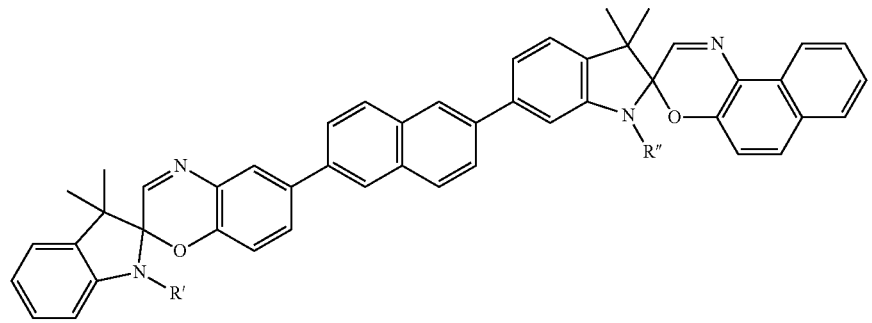

wherein, R' and R" independently represent hydrogen, a halogen, a substituted or unsubstituted $C_{1-8}$ alkyl, or a substituted or unsubstituted $C_{1-8}$ alkoxy. Specifically, R' and R" independently represent hydrogen, a halogen, a substituted or unsubstituted $C_{1-6}$ alkyl, or a substituted or unsubstituted $C_{1-6}$ alkoxy.

III. Articles Incorporating Photochromic Dyes

This disclosure also provides a photochromic composition. The photochromic composition can include one or more of the photochromic dyes described previously herein, with the dye (or dyes) being incorporated into a portion of a first material. In illustrative embodiments, the material may include, but is not limited to, a polymer, a biopolymer such as DNA/RNA or protein, an oligomer, a monomer or a mixture or combination thereof.

The photochromic dye may be incorporated into a portion of a material, such as a polymer, oligomer or monomer to form a photochromic composition, which may be used, for example and without limitation, to form photochromic articles. As used herein the term "polymer" refers to homopolymers and copolymers as well as blends and other combinations thereof. As used herein the terms "oligomer" refer to a combination of two or more monomer units that is capable of reacting with additional monomer units. As used herein the term "incorporated into" means physically and/or chemically combined with. For example, the photochromic dyes according to various non-limiting examples disclosed herein may be physically associated with a portion of an material, for example and without limitation, by mixing, combining, impregnating, inserting, or imbibing the photochromic dye into the material; and/or chemically combined with a portion of a material, for example and without limitation, by copolymerization or otherwise bonding (e.g., covalently or non-covalently linking) the photochromic dye to the material.

According to various non-limiting embodiments disclosed herein, the photochromic dye may be incorporated into a portion of the material by at least one of blending and bonding the photochromic dye with the material. As used herein with reference to the incorporation of photochromic dyes into a material, the terms "blending" and "blended" mean that the photochromic dye is intermixed or intermingled with a portion of the material, but not bonded to the material. Further, as used herein with reference to the incorporation of photochromic dyes into a material, the terms "bonding" or "bonded" mean that the photochromic dye is linked to a portion of the material. For example, although not limiting herein, the photochromic dye may be linked to the material through a reactive substituent.

According to one embodiment, the photochromic dye may be incorporated into a portion of a material at a rate from about 0.001 wt % to about 5.0 wt %, or about 0.01 wt % to about 4.5 wt %, or about 0.1 wt % to about 4.0 wt %, or about 0.2 wt % to about 3.5 wt %, or about 0.5 wt % to about 3.0 wt %, or about 1.0 wt % to about 2.0 wt %, or about 1.2 wt % to about 1.7 wt %, or about 1.5 wt %.

According to one specific non-limiting embodiment, the material may be a polymeric material at least one selected from the group consisting of polyacrylates, polymethacrylates, poly(C1-C12) alkyl methacrylates, polyoxy(alkylene methacrylates), poly(alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), poly(vinylpyrrolidone), poly((meth)acrylamide), poly(dimethyl acrylamide), poly(hydroxyethyl methacrylate), poly((meth)acrylic acid), thermoplastic polycarbonates, polyesters, polyurethanes, polythiourethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of polyol(allyl carbonate)monomers, mono-functional acrylate monomers, mono-functional methacrylate monomers, polyfunctional acrylate monomers, polyfunctional methacrylate monomers, diethylene glycol dimethacrylate monomers, diisopropenyl benzene monomers, alkoxylated polyhydric alcohol monomers and diallylidene pentaerythritol monomers.

In general, glass transition temperature ($T_g$) refers to the temperature at which a polymer or another material transitions from a rigid, solid state to a pliable state. For example, polymers having glass transition temperatures well below room temperature can be characterized as elastomers and/or viscous liquids, whereas polymers having glass transition temperatures well above room temperature can be characterized as rigid, structural polymers.

Because the transition of photochromic dyes from one state to another generally involves one or more structural rearrangements, the switching speed of photochromic dyes can be sensitive to the rigidity of the environment around the dye. As a result, photochromic dyes switch most rapidly in solution and slowest in the rigid environment like in rigid polymer. One way that switching speeds can be increased is to incorporate the dyes into a low $T_g$ polymer (e.g., a polymer having a glass transition temperature well below room temperature). The low $T_g$ polymer can then be incorporated into a rigid material for structure while preserving the reduced switching speed afforded by the non-rigid material. Attaching flexible, low $T_g$ polymers to photochromic dyes can allow them to switch much more rapidly in a rigid matrix. For example, some spirooxazines with siloxane polymers attached can switch at near solution-like speeds even though they are incorporated into a rigid matrix.

As such, in one embodiment, the dye can be incorporated into at least one material having a glass transition temperature less than about 0° C., or less than about −5° C., or less than about −10° C., or less than about −15° C., or less than about −20° C., or less than about −25° C., or less than about −30° C., or less than about −35° C., or less than about −40° C., or less than about −45° C., or less than about −50° C., or less than about −55° C., or less than about −60° C.

In another embodiment, the dye can be incorporated into a second material, which can then be incorporated into the first material discussed above, where the second material has a glass transition temperature less than about 0° C., or less than about −5° C., or less than about −10° C., or less than about −15° C., or less than about −20° C., or less than about −25° C., or less than about −30° C., or less than about −35° C., or less than about −40° C., or less than about −45° C., or less than about −50° C., or less than about −55° C., or less than about −60° C.

In yet another embodiment, photochromic dye can be incorporated into a second material selected from the group consisting of a polysiloxane and/or a polyacrylate having a glass transition temperature less than about 0° C., or less than about −5° C., or less than about −10° C., or less than about −15° C., or less than about −20° C., or less than about −25° C., or less than about −30° C., or less than about −35° C., or less than about −40° C., or less than about −45° C., or less than about −50° C., or less than about −55° C., or less than about −60° C. As discussed above, the second material including the dye can be incorporated into the first material.

A non-limiting example of a polyacrylate having a glass transition temperature less than about 0° C. is poly(butyl acrylate), which has a glass transition temperature of −49° C. Polymerized siloxanes with organic side chains (R≠H) are commonly known as silicones or as polysiloxanes. Representative examples include, but are not limited to, $[SiO(CH_3)_2]n$ (polydimethylsiloxane) ("PDMS") and $[SiO(C_6H_5)_2]n$ (polydiphenylsiloxane). These compounds can be viewed as a hybrid of both organic and inorganic compounds. The organic side chains confer hydrophobic properties while the —Si—O—Si—O— backbone is purely inorganic.

PDMS is a widely used silicon-based organic polymer. Its applications range from contact lenses and medical devices to elastomers. PDMS is viscoelastic, meaning that at long flow times (or high temperatures), it acts like a viscous liquid, similar to honey. However at short flow times (or low temperatures) it acts like an elastic solid, similar to rubber. Due to its unique mechanical, chemical, and optical properties, PDMS is integrated into many optical devices. PDMS is optically clear at a wide range of wavelengths. In addition, the curing time and temperature used during cross-linking (generally with methyltrichlorosilane) can determine the refractive index (RI) of the bulk. Since the polymer can be easily molded, it has been used to form lenses and waveguides. Also, the effective RI and absorption spectrum of PDMS are changed when organic compounds are physically absorbed into the polymer.

In another embodiment, the present disclosure provides an optical article that is made of and/or incorporates one or more of the photochromic dyes or compositions disclosed herein. According to one aspect, an optical article can include at least one optical article, and at least one photochromic dye incorporated into at least a portion of the optical article.

As used herein the term "optical" means pertaining to or associated with light and/or vision. The optical elements according to various non-limiting embodiments disclosed herein may include, without limitation, ophthalmic elements, display elements, windows, mirrors, and liquid crystal cell elements. As used herein the term "ophthalmic" means pertaining to or associated with the eye and vision. Non-limiting examples of ophthalmic elements include corrective and non-corrective lenses, including single vision or multi-vision lenses, which may be either segmented or non-segmented multi-vision lenses (such as, but not limited to, bifocal lenses, trifocal lenses and progressive lenses), contact lenses, as well as other elements used to correct, protect, or enhance (cosmetically or otherwise) vision, including without limitation, magnifying lenses, protective lenses, visors, goggles, as well as, lenses for optical instruments (for example, cameras and telescopes). As used herein the term "display" means the visible or machine-readable representation of information in words, numbers, symbols, designs or drawings. Non-limiting examples of display elements include screens, monitors, and security elements, such as security marks. As used herein the term "window" means an aperture adapted to permit the transmission of radiation therethrough. Non-limiting examples of windows include automotive and aircraft transparencies, windshields, filters, shutters, and optical switches. As used herein the term "mirror" means a surface that specularly reflects a large fraction of incident light. As used herein the term "liquid crystal cell" refers to a structure containing a liquid crystal material that is capable of being ordered. One non-limiting example of a liquid crystal cell element is a liquid crystal display.

In one embodiment, the photochromic dye incorporated into the optical article can include a first photo-reactive group and a second photo-reactive group. In one aspect, a first photochromic reaction can be induced in the first photo-reactive group by radiation having a first intensity, and a second photochromic reaction can be induced in the second photo-reactive group by radiation having a second intensity. Any of the other photochromic dyes described herein can be incorporated in the optical article without limitation as to composition.

In one aspect, the optical article can be fabricated from or further include at least one polymer selected from the group consisting of polyacrylates, polymethacrylates, polyalkylmethacrylates, polyoxy(alkylene methacrylates), poly (alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), poly(vinylpyrrolidone), poly((meth)acrylamide), poly(dimethyl acrylamide), poly (hydroxyethyl methacrylate), poly((meth)acrylic acid), thermoplastic polycarbonates, polyesters, polyurethanes, polythiourethanes, poly(ethylene terephthalate), polystyrene, poly(alpha methylstyrene), copoly(styrene-methylmethacrylate), copoly(styrene-acrylonitrile), polyvinylbutyral, and polymers of members of the group consisting of polyol(allyl carbonate)monomers, mono-functional acrylate monomers, mono-functional methacrylate monomers, polyfunctional acrylate monomers, polyfunctional methacrylate monomers, diethylene glycol dimethacrylate monomers, diisopropenyl benzene monomers, alkoxylated polyhydric alcohol monomers and diallylidene pentaerythritol monomers.

As described above, the dye incorporated in the optical article can be incorporated into at least one material having a glass transition temperature less than about 0° C. In another aspect, the dye can be incorporated into a second material, which can then be incorporated into the first material discussed above, where the second material has a glass transition temperature less than about 0° C. In yet another embodiment, photochromic dye can be incorporated into a second material selected from the group consisting of a polysiloxane and/or a polyacrylate having a glass transition temperature less than about 0° C.

Various non-limiting embodiments disclosed herein provide photochromic articles comprising a substrate and a photochromic dye according to any of the non-limiting embodiments discussed above connected to a portion of the substrate. As used herein, the term "connected to" means associated with, either directly or indirectly through another material or structure.

Non-limiting embodiments disclosed herein provide a method of preparing an optical element, comprising connecting a photochromic composition to at least a portion of a substrate by at least one of in-mold casting, coating and lamination.

For example, according to one non-limiting embodiment, the photochromic composition may be connected to at least a portion of a substrate by in-mold casting. According to this non-limiting embodiment, a coating composition comprising the photochromic composition, which may be a liquid coating composition or a powder coating composition, is applied to the surface of a mold. After that, the coated substrate is removed from the mold. Non-limiting examples of powder coatings in which the photochromic composition according to various non-limiting embodiments disclosed herein may be employed are set forth in U.S. Pat. No. 6,068,797, the disclosure of which is incorporated by reference herein in its entirety.

According to another non-limiting embodiment, the photochromic composition may be connected to a portion of a substrate by coating. Non-limiting examples of suitable coating methods include spin coating, spray coating (e.g., using a liquid or powder coating), curtain coating, roll coating, spin and spray coating, over-molding, and combinations thereof. For example, according to one non-limiting embodiment, the photochromic composition may be connected to the substrate by over-molding. According to this non-limiting embodiment, a coating composition comprising the photochromic composition (which may be a liquid coating composition or a powder coating composition as previously discussed) may be applied to a mold and then the substrate may be placed into the mold such that the substrate contacts the coating causing it to spread over the surface of the substrate. Thereafter, the coating composition may be at least partially set and the coated substrate may be removed from the mold. As used herein, the term "set" include, without limitation, curing, polymerizing, cross-linking, cooling, and drying. Alternatively, over-molding may be done by placing the substrate into a mold such that an open region is defined between the substrate and the mold, and thereafter injecting a coating composition comprising the photochromic composition into the open region. Thereafter, the coating composition may be at least partially set and the coated substrate may be removed from the mold.

Additionally or alternatively, a coating composition (with or without a photochromic composition) may be applied to a substrate (for example, by any of the foregoing methods), the coating composition may be at least partially set, and thereafter, a photochromic dye may be imbibed (as previously discussed) into the coating composition.

According to still another non-limiting embodiment, wherein the substrate comprises a polymeric material or an inorganic material such as glass, the photochromic composition may be connected to at least a portion of a substrate by lamination. According to this non-limiting embodiment, a film comprising the photochromic composition may be adhered or otherwise connect to at least a portion of the substrate, with or without an adhesive and/or the application of heat and pressure. Thereafter, if desired, a second substrate may be applied over the first substrate and the two substrates may be laminated together (i.e., by the application of heat and pressure) to form an element wherein the film comprising the photochromic composition is interposed between the two substrates. Methods of forming films comprising a photochromic composition may include, for example and without limitation, combining a photochromic composition with a polymeric solution or oligomeric solution or mixture, casting or extruding a film therefrom, and, if required, at least partially setting the film. Additionally or alternatively, a film may be formed (with or without a photochromic composition) and imbibed with the photochromic composition (as discussed above).

Further, it will be appreciated by those skilled in the art that the photochromic compositions and articles according to various non-limiting embodiments disclosed herein may further comprise other additives that aid in the processing and/or performance of the composition or article. Non-limiting examples of such additives include from photoinitiators, thermal initiators, polymerization inhibitors, solvents, light stabilizers (such as, but not limited to, ultraviolet light absorbers and light stabilizers, such as hindered amine light stabilizers (HALS)), heat stabilizers, mold release agents, rheology control agents, leveling agents (such as, but not limited to, surfactants), free radical scavengers, adhesion promoters (such as hexanediol diacrylate and coupling agents), and combinations and mixtures thereof.

The present disclosure is not to be limited in terms of the particular examples described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular examples only, and is not intended to be limiting.

With respect to the use of substantially any plural and/or singular terms herein, those having skill in the art can translate from the plural to the singular and/or from the singular to the plural as is appropriate to the context and/or application.

The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description or claims, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth."

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

EXAMPLES

The synthesis procedures used to make photochromic dyes according to various non-limiting embodiments disclosed herein are set forth in Examples 1 to 2.

Example 1

The synthesis of 1,3,3-trimethyl-6-(4-(1',3',3'-trimethylspiro[benzo[b][1,4]oxazine-2,2'-indoline]-6-yl)phenyl)spiro[indoline-2,3'-naphtho[2,1-b][1,4]oxazine]

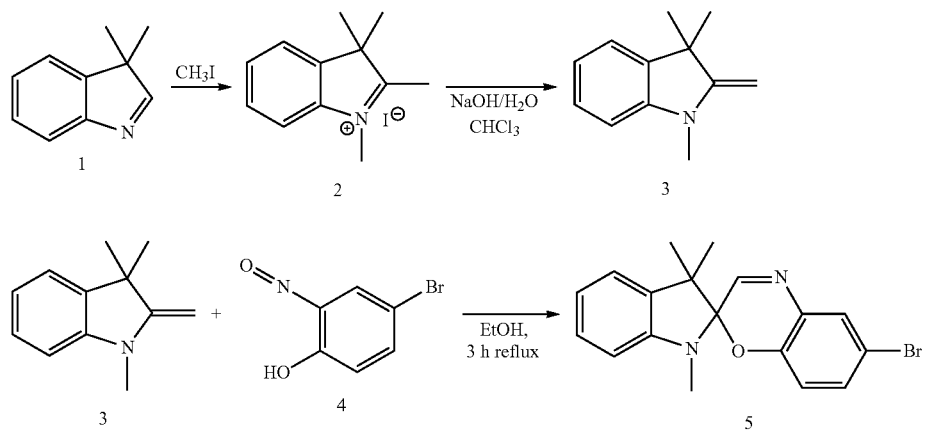

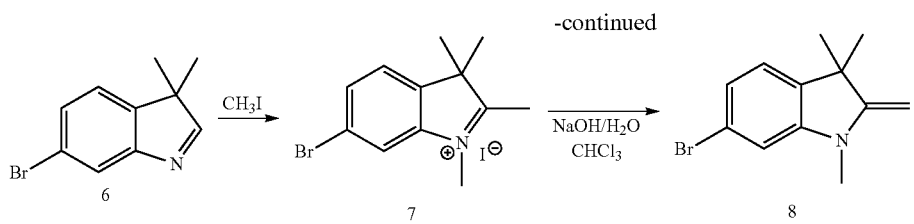

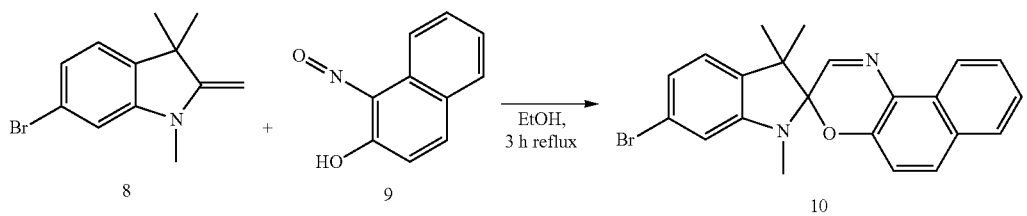

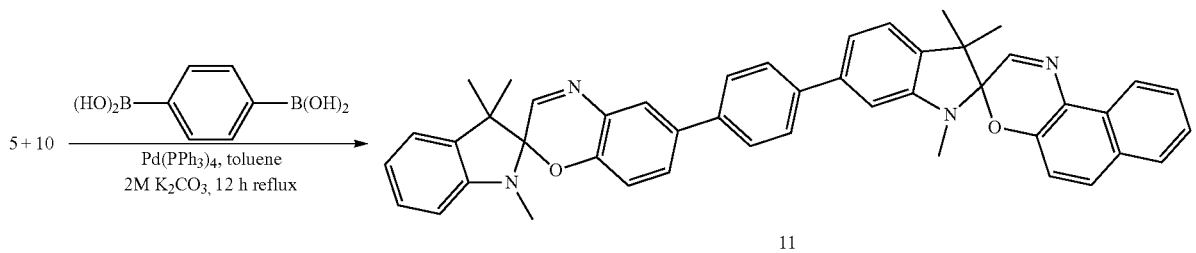

Preparation of compound 2: A solution of 2,3,3-trimethyl-3H-indole and iodomethane in dichloroethane is refluxed by stirring for 4 h. Then the reaction mixture is stirred for one hour at room temperature and the precipitated solid is collected by filtration.

Preparation of compound 3: After the crude solid of compound 2 is washed with acetone, a portion of the solid is dissolved in NaOH aqueous solution (1 M). The resultant 1,3,3-trimethyl-2-methyleneindoline is extracted with chloroform. The organic layer is dried with anhydrous Na$_2$SO$_4$ and the solvent was evaporated.

Preparation of compound 5: Compound 3 and 4-bromo2-nitrosophenol are dissolved in ethanol and the mixture is stirred at 90° C. for 3 h. After cooling the mixture, the solid product, 5 is obtained by filtration.

Preparation of compound 7: A solution of 6-bromo-2,3,3-trimethyl-3H-indole and iodomethane in dichloroethane is refluxed by stirring for 6 h. Then the reaction mixture is stirred for one hour at room temperature and the precipitated solid, 7 is collected by filtration.

Preparation of compound 8: After the solid of compound 7 is washed with acetone, a portion of the solid is dissolved in NaOH aqueous solution (1 M). The resultant 6-bromo-1,3,3-trimethyl-2-methyleneindoline, 8 is extracted with chloroform. The organic layer is dried with anhydrous Na$_2$SO$_4$ and the solvent is evaporated. The product is obtained in a fairly high yield.

Preparation of compound 10: compound 8 and 1-nitrosonaphtalen-2-ol are dissolved in ethanol and the mixture is stirred at 90° C. for 3 h. After cooling the mixture, the solid product, 6-bromo-1,3,3-trimethylspiro[indoline-2,3'-naphtho[2,1-b][1,4]oxazine] is obtained by filtration.

Preparation of compound 11: Suzuki coupling Reaction

Compound 5 and 10 are dissolved in toluene with the presence of 1,4-phenylenediboronic acid, Pd(PPh$_3$)$_4$, K$_2$CO$_3$. The mixture is refluxed for 12 hrs. The final compound, 1,3,3-trimethyl-6-(4-(1',3',3'-trimethylspiro[benzo[b][1,4]oxazine-2,2'-indoline]-6-yl)phenyl)spiro[indoline-2,3'-naphtho[2,1-b][1,4]oxazine] is obtained by silical gel chromatography (EA:hexane=1:2). The resultant compound is purified by reprecipitation in THF/hexane.

Example 2

The synthesis of (E)-1,3,3-trimethyl-6-(2-(1',3',3'-trimethylspiro[benzo[b][1,4]oxazine-2,2'-indoline]-6-yl)vinyl)spiro[indoline-2,3'-naphtho[2,1-b][1,4]oxazine]

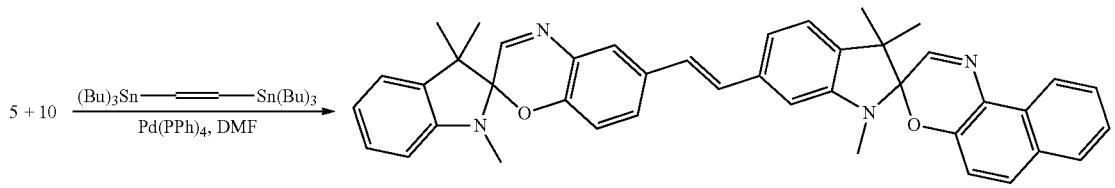

The synthesis of compound 12 is quite similar to that of compound 11.

Compound 5 and 10 are dissolved in dimethylformamide with the presence of 1,2-bis(tributylstannyl)ethane, Pd (PPh$_3$)$_4$. The reaction mixture is refluxed for overnight. The final compound, (E)-1,3,3-trimethyl-6-(2-(1',3',3'-trimethyl-spiro[benzo[b][1,4]oxazine-2,2'-indoline]-6-yl)vinyl)spiro [indoline-2,3'-naphtho[2,1-b][1,4]oxazine] is obtained by silical gel chromatography (EA:hexane=1:4). The resultant compound is purified by reprecipitation in THF/hexane.

What is claimed is:

1. A photochromic dye, comprising:
    at least a first photo-reactive group and a second photo-reactive group, wherein
        the first photo-reactive group is configured to undergo a first photochromic reaction responsive to radiation having a first intensity;
        the second photo-reactive group is configured to undergo a second photochromic reaction responsive to radiation having a second intensity, wherein the second intensity is different than the first intensity; and
    wherein the photochromic dye is represented by a structure of Formula I:

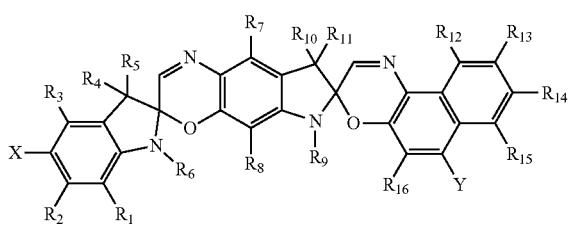

[Formula I]

wherein,
    X and Y independently represent hydrogen, an electron donor group selected from the group consisting of an amino, an alkylamino, a dialkylamino, an alkyl, an alkoxy, a julolidine or a diphenyl, and combinations thereof or an electron acceptor group selected from the group consisting of a cyano, a nitrogen oxide, a halogen, a trifluoromethyl, a dicyanovinyl or a tricyanovinyl, and combinations thereof, but if X represents an electron donor group then Y represents hydrogen or an electron acceptor group, and if X represents an electron acceptor group then Y represents hydrogen or an electron donor group; and
    R1 to R16 independently represent hydrogen, a halogen, a substituted or unsubstituted C1-8 alkyl, a substituted or unsubstituted C1-8 alkoxy, a substituted or unsubstituted C1-8 alkenyl, a substituted or unsubstituted C1-8 conjugated alkyl, a substituted or unsubstituted aryl group, a substituted or unsubstituted heteroaryl group, or the substituents together form an alkylene or alkenylene chain completing an aryl group.

2. The photochromic dye of claim 1, wherein the first photo-reactive group is configured to undergo the first photochromic reaction before the second photo-reactive group undergoes the second photochromic reaction.

3. The photochromic dye of claim 2, wherein the second intensity is greater than the first intensity.

4. The photochromic dye of claim 1, wherein
    the first photo-reactive group has a first conjugation system and the second photo-reactive group has a second conjugation system; and wherein
    the first conjugation system is achieved when the first photochromic reaction is induced, and the second conjugation system is achieved when the second photochromic reaction is induced.

5. The photochromic dye of claim 4, wherein the first conjugation system has a first conjugation bond length and the second conjugation system has a second conjugation bond length that is longer than the first conjugation bond length.

6. The photochromic dye of claim 1, wherein the difference of molar absorptivity between the first photo-reactive group and the second photo-reactive group is greater than or equal to about 5000 L/mol.

7. The photochromic dye of claim 1, wherein the first photochromic reaction is induced when light having an intensity of about 50 mW/cm$^2$ to about 100 mW/cm$^2$ is absorbed by the first photo-reactive group, and the second photochromic reaction is induced when light having an intensity of about 150 mW/cm$^2$ to about 200 mW/cm$^2$ is absorbed by the second photo-reactive group.

8. The photochromic dye of claim 1, wherein the first and the second photo-reactive groups are each at least one of the group consisting of a spiropyran compound, a spirooxazine compound, a diarylethene compound and a fulgide compound.

9. The photochromic dye of claim 1 wherein the dye of Formula I is selected from the group consisting of Formula I-1 to I-8 and combinations thereof:

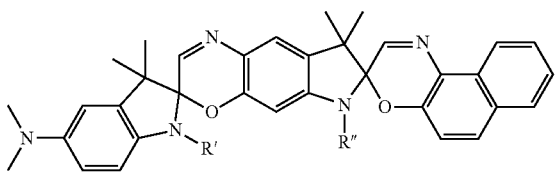

[Formula I-1]

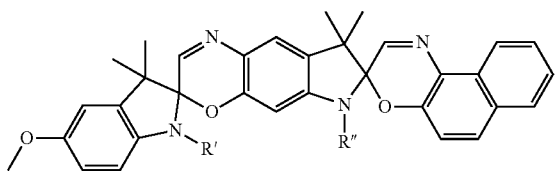

[Formula I-2]

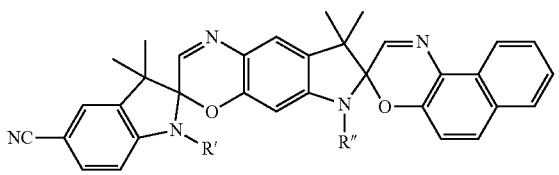

[Formula I-3]

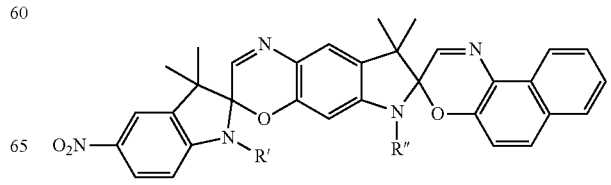

[Formula I-4]

[Formula I-5]

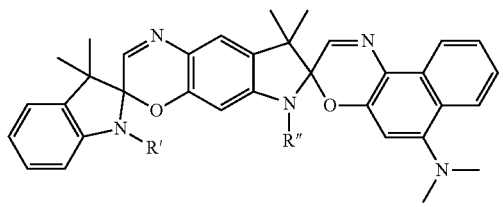

[Formula I-6]

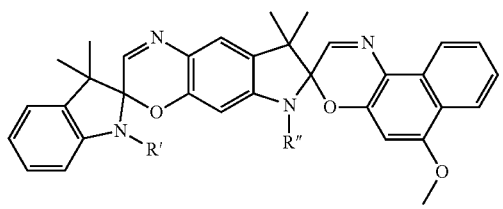

[Formula I-7]

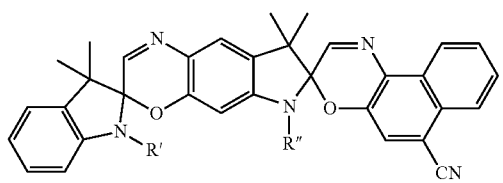

[Formula I-8]

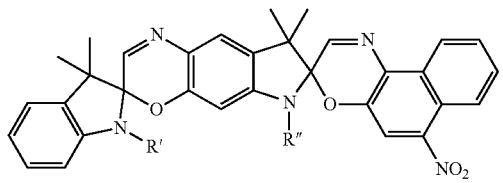

wherein,

R' and R" independently represent hydrogen, a halogen, a substituted or unsubstituted $C_{1-8}$ alkyl, or a substituted or unsubstituted $C_{1-8}$ alkoxy.

10. A photochromic composition, comprising:
at least one material selected from the group consisting of a polymer, an oligomer, a monomer, or a mixture thereof;
at least one photochromic dye incorporated into at least a portion of the material, wherein the at least one photochromic dye includes:
a first photo-reactive group and a second photo-reactive group, wherein
a first photochromic reaction is induced in the first photo-reactive group responsive to radiation having a first intensity;
a second photochromic reaction is induced in the second photo-reactive group responsive to radiation having a second intensity; and
wherein the at least one photochromic dye is represented by a structure of Formula I:

[Formula I]

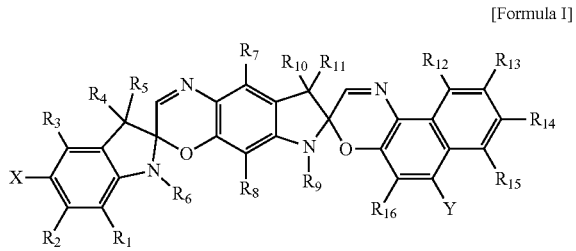

wherein,
X and Y independently represent hydrogen, an electron donor group selected from the group consisting of an amino, an alkylamino, a dialkylamino, an alkyl, an alkoxy, a julolidine or a diphenyl, and combinations thereof or an electron acceptor group selected from the group consisting of a cyano, a nitrogen oxide, a halogen, a trifluoromethyl, a dicyanovinyl or a tricyanovinyl, and combinations thereof, but if X represents an electron donor group then Y represents hydrogen or an electron acceptor group, and if X represents an electron acceptor group then Y represents hydrogen or an electron donor group; and
R1 to R16 independently represent hydrogen, a halogen, a substituted or unsubstituted C1-8 alkyl, a substituted or unsubstituted C1-8 alkoxy, a substituted or unsubstituted C1-8 alkenyl, a substituted or unsubstituted C1-8 conjugated alkyl, a substituted or unsubstituted aryl group, a substituted or unsubstituted heteroaryl group, or the substituents together form an alkylene or alkenylene chain completing an aryl group.

11. The photochromic composition of claim 10, wherein the at least one material is at least one polymer one selected from the group consisting of polyacrylates, polymethacrylates, polyalkylmethacrylates, polyoxy(alkylene methacrylates), poly(alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), poly (vinylpyrrolidone), poly((meth)acrylamide), poly(dimethyl acrylamide), poly(hydroxyethyl methacrylate), poly((meth) acrylic acid), thermoplastic polycarbonates, polyesters, polyurethanes, polythiourethanes, poly(ethylene terephthalate), polystyrene, poly(alpha methylstyrene), copoly(styrene-methylmethacrylate), copoly(styrene-acrylonitrile), polyvinylbutyral, and polymers of members of the group consisting of polyol(allyl carbonate)monomers, mono-functional acrylate monomers, mono-functional methacrylate monomers, polyfunctional acrylate monomers, polyfunctional methacrylate monomers, diethylene glycol dimethacrylate monomers, diisopropenyl benzene monomers, alkoxylated polyhydric alcohol monomers and diallylidene pentaerythritol monomers.

12. The photochromic composition of claim 10, wherein the at least one material further includes at least a second material having a glass transition temperature less than about 0° C.

13. The photochromic composition of claim 12, wherein the dye is coupled to the second material by at least one covalent linkage.

14. The photochromic composition of claim 10, wherein the first and the second photo-reactive groups are each selected from the group consisting of a spiropyran compound, a spirooxazine compound, a diarylethene compound, a fulgide compound, and combinations thereof.

15. An article, comprising:
   at least one optical article selected from the group consisting of ophthalmic elements, display elements, windows, mirrors, liquid crystal cell elements, and combinations thereof;
   at least one photochromic dye incorporated into at least a portion of the optical article, wherein the at least one photochromic dye includes:
      a first photo-reactive group and a second photo-reactive group, wherein
         a first photochromic reaction is induced in the first photo-reactive group responsive to radiation having a first intensity;
         a second photochromic reaction is induced in the second photo-reactive group responsive to radiation having a second intensity; and
      wherein the at least one photochromic dye is represented by a structure of Formula I:

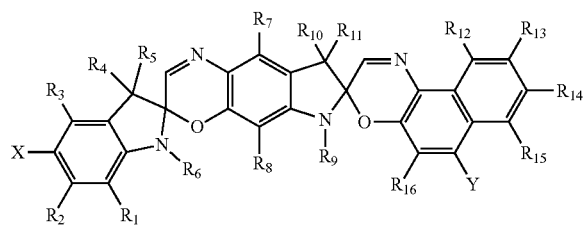

[Formula I]

wherein,
   X and Y independently represent hydrogen, an electron donor group selected from the group consisting of an amino, an alkylamino, a dialkylamino, an alkyl, an alkoxy, a julolidine or a diphenyl, and combinations thereof or an electron acceptor group selected from the group consisting of a cyano, a nitrogen oxide, a halogen, a trifluoromethyl, a dicyanovinyl or a tricyanovinyl, and combinations thereof, but if X represents an electron donor group then Y represents hydrogen or an electron acceptor group, and if X represents an electron acceptor group then Y represents hydrogen or an electron donor group; and
   $R_1$ to $R_{16}$ independently represent hydrogen, a halogen, a substituted or unsubstituted C1-8 alkyl, a substituted or unsubstituted C1-8 alkoxy, a substituted or unsubstituted C1-8 alkenyl, a substituted or unsubstituted C1-8 conjugated alkyl, a substituted or unsubstituted aryl group, a substituted or unsubstituted heteroaryl group, or the substituents together form an alkylene or alkenylene chain completing an aryl group.

16. The article of claim 15, wherein the optical article further includes at least one polymer selected from the group consisting of polyacrylates, polymethacrylates, polyalkylmethacrylates, polyoxy(alkylene methacrylates), poly(alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), poly(vinylpyrrolidone), poly((meth)acrylamide), poly(dimethyl acrylamide), poly(hydroxyethyl methacrylate), poly((meth)acrylic acid), thermoplastic polycarbonates, polyesters, polyurethanes, polythiourethanes, poly(ethylene terephthalate), polystyrene, poly(alpha methylstyrene), copoly(styrene-methylmethacrylate), copoly(styrene-acrylonitrile), polyvinylbutyral, and polymers of members of the group consisting of polyol(allyl carbonate)monomers, mono-functional acrylate monomers, mono-functional methacrylate monomers, polyfunctional acrylate monomers, polyfunctional methacrylate monomers, diethylene glycol dimethacrylate monomers, diisopropenyl benzene monomers, alkoxylated polyhydric alcohol monomers and diallylidene pentaerythritol monomers.

17. The article of claim 15, wherein the first and the second photo-reactive groups are each selected from the group consisting of a spiropyran compound, a spirooxazine compound, a diarylethene compound, a fulgide compound, and combinations thereof.

18. A photochromic dye, comprising:
   at least a first photo-reactive group and a second photo-reactive group, wherein
      the first photo-reactive group is configured to undergo a first photochromic reaction responsive to radiation having a first intensity;
      the second photo-reactive group is configured to undergo a second photochromic reaction responsive to radiation having a second intensity, wherein the second intensity is different than the first intensity; and
   wherein the photochromic dye is represented by a structure of Formula II:

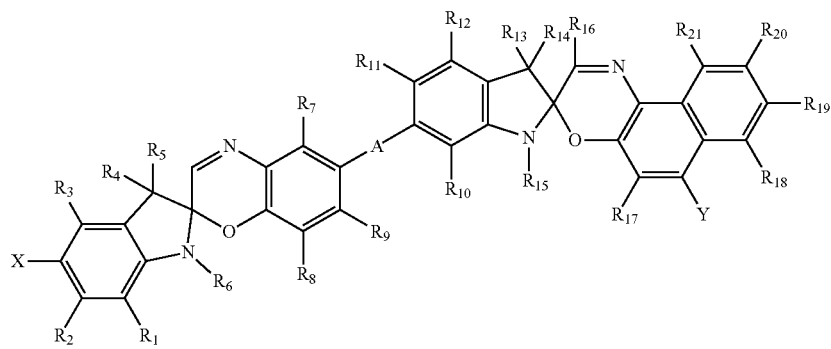

[Formula II]

wherein,

X and Y independently represent hydrogen, an electron donor group or an electron acceptor group, but if X represents an electron donor group then Y represents hydrogen or an electron acceptor group, and if X represents an electron acceptor group then Y represents hydrogen or an electron donor group;

$R_1$ to $R_{21}$ independently represent hydrogen, a halogen, a substituted or unsubstituted $C_{1-8}$ alkyl, a substituted or unsubstituted $C_{1-8}$ alkoxy, a substituted or unsubstituted $C_{1-8}$ alkenyl, a substituted or unsubstituted $C_{1-8}$ conjugated alkyl, a substituted or unsubstituted aryl group, a substituted or unsubstituted heteroaryl group, or the substituents together form an alkylene or alkenylene chain completing an aryl group; and A represents a single bond,

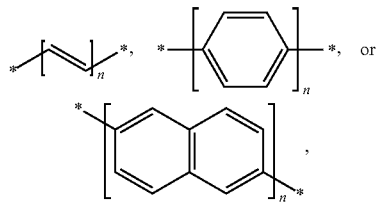

wherein n is 1 to 6.

19. The photochromic dye of claim 18, wherein the dye of Formula II is selected from the group consisting of Formula II-1 to II-4 and combinations thereof:

[Formula II-1]

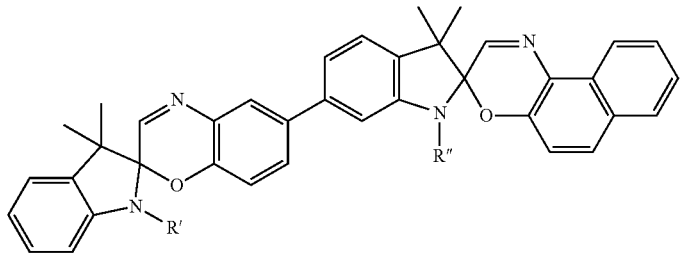

[Formula II-2]

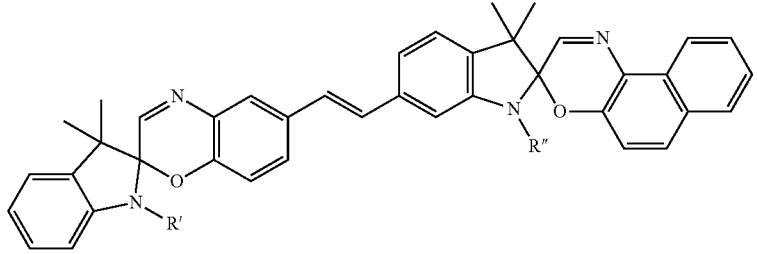

[Formula II-3]

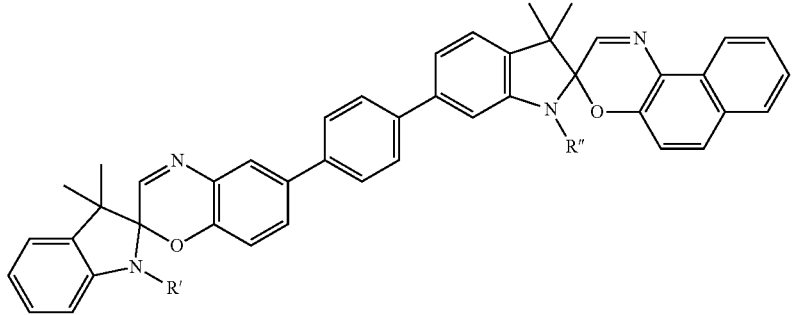

[Formula II-4]

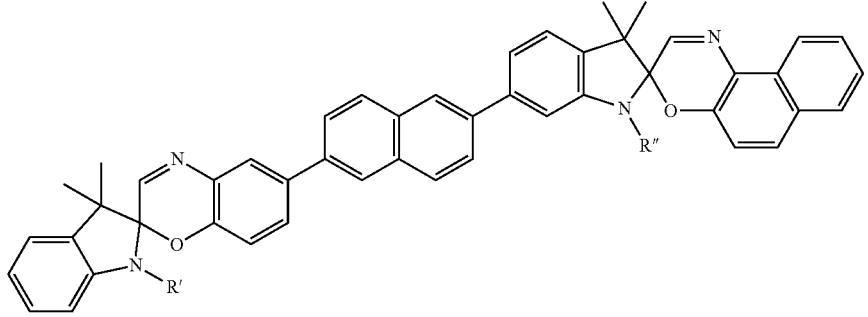

wherein,
R' and R" independently represent hydrogen, a halogen, a substituted or unsubstituted $C_{1-8}$ alkyl, or a substituted or unsubstituted $C_{1-8}$ alkoxy.

20. The photochromic dye of claim 18, wherein the first photo-reactive group is configured to undergo the first photochromic reaction before the second photo-reactive group undergoes the second photochromic reaction.

21. The photochromic dye of claim 20, wherein the second intensity is greater than the first intensity.

22. The photochromic dye of claim 18, wherein
the first photo-reactive group has a first conjugation system and the second photo-reactive group has a second conjugation system, and wherein
the first conjugation system is achieved when the first photochromic reaction is induced,
and the second conjugation system is achieved when the second photochromic reaction is induced.

23. The photochromic dye of claim 22, wherein the first conjugation system has a first conjugation bond length and the second conjugation system has a second conjugation bond length that is longer than the first conjugation bond length.

24. The photochromic dye of claim 18, wherein the difference of molar absorptivity between the first photo-reactive group and the second photo-reactive group is greater than or equal to about 5000 L/mol.

25. The photochromic dye of claim 18, wherein the first photochromic reaction is induced when light having an intensity of about 50 mW/cm² to about 100 mW/cm² is absorbed by the first photo-reactive group, and the second photochromic reaction is induced when light having an intensity of about 150 mW/cm² to about 200 mW/cm² is absorbed by the second photo-reactive group.

26. The photochromic dye of claim 18, wherein the first and the second photo-reactive groups are each at least one of the group consisting of a spiropyran compound, a spirooxazine compound, a diarylethene compound and a fulgide compound.

27. A photochromic composition, comprising:
at least one material selected from the group consisting of a polymer, an oligomer, a monomer, or a mixture thereof;
at least one photochromic dye incorporated into at least a portion of the material, wherein the at least one photochromic dye includes:
a first photo-reactive group and a second photo-reactive group, wherein
a first photochromic reaction is induced in the first photo-reactive group responsive to radiation having a first intensity;
a second photochromic reaction is induced in the second photo-reactive group responsive to radiation having a second intensity; and
wherein the photochromic dye is represented by a structure of Formula II:

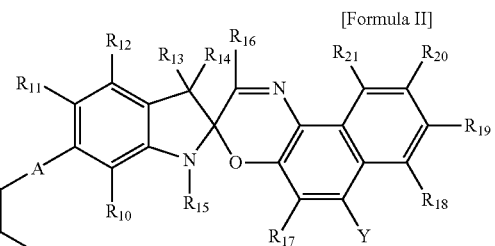

wherein,
X and Y independently represent hydrogen, an electron donor group or an electron acceptor group, but if X represents an electron donor group then Y represents hydrogen or an electron acceptor group, and if X represents an electron acceptor group then Y represents hydrogen or an electron donor group;
$R_1$ to $R_{21}$ independently represent hydrogen, a halogen, a substituted or unsubstituted $C_{1-8}$ alkyl, a substituted or unsubstituted $C_{1-8}$ alkoxy, a substituted or unsubstituted $C_{1-8}$ alkenyl, a substituted or unsubstituted $C_{1-8}$ conjugated alkyl, a substituted or unsubstituted aryl group, a substituted or unsubstituted heteroaryl group, or the substituents together form an alkylene or alkenylene chain completing an aryl group; and
A represents a single bond,

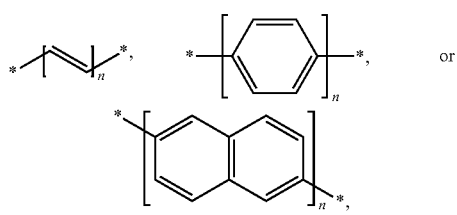

wherein n is 1 to 6.

28. An article, comprising:
at least one optical article selected from the group consisting of ophthalmic elements, display elements, windows, mirrors, liquid crystal cell elements, and combinations thereof;
at least one photochromic dye incorporated into at least a portion of the optical article, wherein the at least one photochromic dye includes:
a first photo-reactive group and a second photo-reactive group, wherein
a first photochromic reaction is induced in the first photo-reactive group responsive to radiation having a first intensity;
a second photochromic reaction is induced in the second photo-reactive group responsive to radiation having a second intensity; and
wherein the photochromic dye is represented by a structure of Formula II:

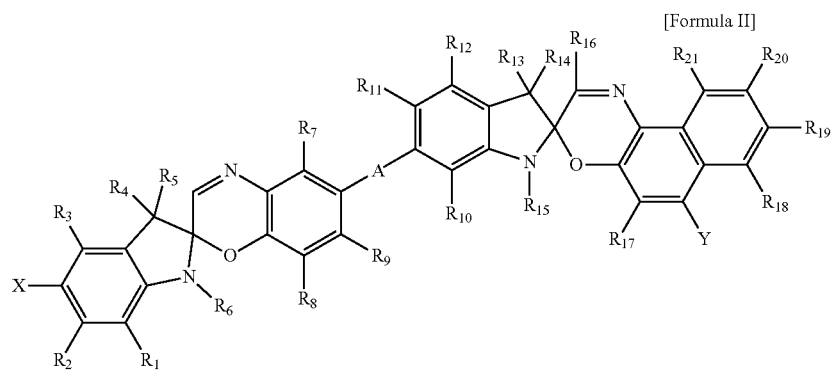

[Formula II]

wherein,

X and Y independently represent hydrogen, an electron donor group or an electron acceptor group, but if X represents an electron donor group then Y represents hydrogen or an electron acceptor group, and if X represents an electron acceptor group then Y represents hydrogen or an electron donor group;

$R_1$ to $R_{21}$ independently represent hydrogen, a halogen, a substituted or unsubstituted $C_{1-8}$ alkyl, a substituted or unsubstituted $C_{1-8}$ alkoxy, a substituted or unsubstituted $C_{1-8}$ alkenyl, a substituted or unsubstituted $C_{1-8}$ conjugated alkyl, a substituted or unsubstituted aryl group, a substituted or unsubstituted heteroaryl group, or the substituents together form an alkylene or alkenylene chain completing an aryl group; and A represents a single bond,

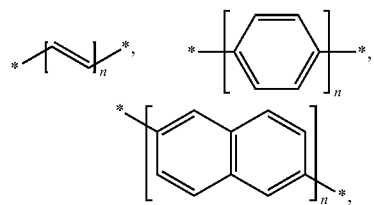

or wherein n is 1 to 6.

* * * * *

UNITED STATES PATENT AND TRADEMARK OFFICE
CERTIFICATE OF CORRECTION

| | |
|---|---|
| PATENT NO. | : 8,287,775 B2 |
| APPLICATION NO. | : 12/707498 |
| DATED | : October 16, 2012 |
| INVENTOR(S) | : Choi |

It is certified that error appears in the above-identified patent and that said Letters Patent is hereby corrected as shown below:

On the Face Page, in Field (56), under "OTHER PUBLICATIONS", in Column 2, Line 15, delete "'Energy" and insert -- "Energy --, therefor.

On the Face Page, in Field (56), under "OTHER PUBLICATIONS", in Column 2, Line 16, delete "Gap'," and insert -- Gap" --, therefor.

On the Face Page, in Field (56), under "OTHER PUBLICATIONS", in Column 2, Lines 20-21, delete "34, No. 10, pp. 119-1121." and insert -- vol. 34, No. 10, pp. 1119-1121. --, therefor.

In Column 9, Line 37, delete "fluoropetenes." and insert -- fluoropentenes --, therefor.

In Column 13, Line 2, delete "in electron" and insert -- electron --, therefor.

In Column 23, Line 57, delete " 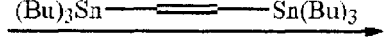 " and insert -- 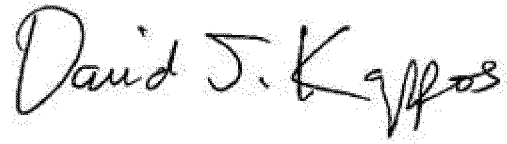 --, therefor.

In Column 25, Line 53, in Claim 1, delete "R1 to R16" and insert -- $R_1$ to $R_{16}$ --, therefor.

In Column 25, Line 54, in Claim 1, delete "C1-8" and insert -- $C_{1-8}$ --, therefor.

In Column 25, Line 55, in Claim 1, delete "C1-8" and insert -- $C_{1-8}$ --, therefor.

In Column 25, Line 56, in Claim 1, delete "C1-8" and insert -- $C_{1-8}$ --, therefor.

Signed and Sealed this
Eighth Day of January, 2013

David J. Kappos
*Director of the United States Patent and Trademark Office*

In Column 25, Line 57, in Claim 1, delete "C1-8" and insert -- $C_{1-8}$ --, therefor.

In Column 26, Line 31, in Claim 9, delete "1" and insert -- 1, --, therefor.

In Column 28, Line 27, in Claim 10, delete "R1 to R16" and insert -- $R_1$ to $R_{16}$ --, therefor.

In Column 28, Line 28, in Claim 10, delete "C1-8" and insert -- $C_{1-8}$ --, therefor.

In Column 28, Line 29, in Claim 10, delete "C1-8" and insert -- $C_{1-8}$ --, therefor.

In Column 28, Line 30, in Claim 10, delete "C1-8" and insert -- $C_{1-8}$ --, therefor.

In Column 28, Line 31, in Claim 10, delete "C1-8" and insert -- $C_{1-8}$ --, therefor.

In Column 29, Line 19, in Claim 15, delete "dve" and insert -- dye --, therefor.

In Column 29, Line 49, in Claim 15, delete "R1 to R16" and insert -- $R_1$ to $R_{16}$ --, therefor.

In Column 29, Line 50, in Claim 15, delete "C1-8" and insert -- $C_{1-8}$ --, therefor.

In Column 30, Line 1, in Claim 15, delete "C1-8" and insert -- $C_{1-8}$ --, therefor.

In Column 30, Line 2, in Claim 15, delete "C1-8" and insert -- $C_{1-8}$ --, therefor.

In Column 30, Line 3, in Claim 15, delete "C1-8" and insert -- $C_{1-8}$ --, therefor.